(12) United States Patent
Gonzales

(10) Patent No.: US 6,314,898 B1
(45) Date of Patent: Nov. 13, 2001

(54) TENSION RELIEVING TOWEL AND METHOD OF MAKING

(76) Inventor: Martin Gonzales, 10733 St. Louis Dr., El Monte, CA (US) 91731

( * ) Notice: Subject to any disclaimer, the term of this patent is extended or adjusted under 35 U.S.C. 154(b) by 0 days.

(21) Appl. No.: 09/535,039

(22) Filed: Mar. 24, 2000

(51) Int. Cl.7 .................................................. D05B 35/00
(52) U.S. Cl. ..................................... 112/475.06; 128/845
(58) Field of Search ......................... 112/475.06, 475.09, 112/147; 2/207, 209.13, 468; 128/845; 602/1, 5

(56) References Cited

U.S. PATENT DOCUMENTS

| | | | |
|---|---|---|---|
| 4,819,622 | 4/1989 | Taylor | 128/75 |
| 4,881,529 | * 11/1989 | Santos . | |
| 4,966,136 | 10/1990 | Bates | 128/87 |
| 5,060,661 | 10/1991 | Howard | 128/845 |
| 6,185,750 | * 2/2001 | Dumas | 2/209.13 |
| 6,209,140 | * 4/2001 | Ebeling | 2/207 |
| 6,226,799 | * 5/2001 | Lane | 2/207 |

* cited by examiner

*Primary Examiner*—Ismael Izaguirre
(74) *Attorney, Agent, or Firm*—Goldstein Law Offices. PC

(57) ABSTRACT

A tension relieving towel and method of making including a rectangular towel having opposed long upper and lower edges and opposed short right and left edges. The towel further includes opposed upper right and left corners and opposed lower right and left corners. The rectangular towel is then laid on a flat recipient surface. Next, fold the upper right and left corners downwardly whereby the upper edge is folded in half within the towel whereby an upper peak is formed. Next, fold the upper peak downwardly. Next, roll the upper peak downwardly about eight revolutions to form a round roll. Next, fold the right side of the towel inwardly. Next, roll the right side of the towel inwardly until meeting the left side to form a seam whereby the round roll forms a cap with a tapered portion extending downwardly therefrom. Lastly, stitch the seam together in a spaced relationship.

2 Claims, 3 Drawing Sheets

TENSION RELIEVING TOWEL AND METHOD OF MAKING

BACKGROUND OF THE INVENTION

The present invention relates to a tension relieving towel and method of making and more particularly pertains to relieving tension in selected body areas.

The use of neck support devices is known in the prior art. More specifically, neck support devices heretofore devised and utilized for the purpose of supporting the neck are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,819,622 to Taylor discloses a neck support collar comprised of folded cloth in the form of a multi-ply pad with Velcro fasteners. U.S. Pat. No. 4,966,136 to Bates discloses a pad covered with fabric to provide orthopedic support to a user. U.S. Pat. No. 5,060,661 to Howard discloses a neck and head support capable of being inflated.

While these devices fulfill their respective, particular objective and requirements, the aforementioned patents do not describe a tension relieving towel and method of making for relieving tension in selected body areas.

In this respect, the tension relieving towel and method of making according to the present invention substantially departs from the conventional concepts and designs of the prior art, and in doing so provides an apparatus primarily developed for the purpose of relieving tension in selected body areas.

Therefore, it can be appreciated that there exists a continuing need for a new and improved tension relieving towel and method of making which can be used for relieving tension in selected body areas. In this regard, the present invention substantially fulfills this need.

SUMMARY OF THE INVENTION

In the view of the foregoing disadvantages inherent in the known types of neck support devices now present in the prior art, the present invention provides an improved tension relieving towel and method of making. As such, the general purpose of the present invention, which will be described subsequently in greater detail, is to provide a new and improved tension relieving towel and method of making which has all the advantages of the prior art and none of the disadvantages.

To attain this, the present invention essentially comprises a rectangular towel having opposed long upper and lower edges and opposed short right and left edges. The towel further includes opposed upper right and left corners and opposed lower right and left corners. The rectangular towel is then laid on a flat recipient surface. Next, fold the upper right and left corners downwardly whereby the upper edge is folded in half within the towel whereby an upper peak is formed. Next, fold the upper peak downwardly. Next, roll the upper peak downwardly about eight revolutions to form a round roll. Next, fold the right side of the towel inwardly. Next, roll the right side of the towel inwardly until meeting the left side to form a seam whereby the round roll forms a cap with a tapered portion extending downwardly therefrom. Lastly, stitch the seam together in a spaced relationship.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tension relieving towel and method of making which has all the advantages of the prior art neck support devices and none of the disadvantages.

It is another object of the present invention to provide a new and improved tension relieving towel and method of making which may be easily and efficiently manufactured and marketed.

It is a further object of the present invention to provide a new and improved tension relieving towel and method of making which is of durable and reliable construction.

An even further object of the present invention is to provide a new and improved tension relieving towel and method of making which is susceptible of a low cost of manufacture with regard to both materials and labor, and which accordingly is then susceptible of low prices of sale to the consuming public, thereby making such a tension relieving towel and method of making economically available to the buying public.

Even still another object of the present invention is to provide a new and improved tension relieving towel and method of making for relieving tension in selected body areas.

Lastly, it is an object of the present invention to provide a new and improved tension relieving towel and method of making including a rectangular towel having opposed long upper and lower edges and opposed short right and left edges. The towel further includes opposed upper right and left corners and opposed lower right and left corners. The rectangular towel is then laid on a flat recipient surface. Next, fold the upper right and left corners downwardly whereby the upper edge is folded in half within the towel whereby an upper peak is formed. Next, fold the upper peak downwardly. Next, roll the upper peak downwardly about eight revolutions to form a round roll. Next, fold the right side of the towel inwardly. Next, roll the right side of the towel inwardly until meeting the left side to form a seam whereby the round roll forms a cap with a tapered portion extending downwardly therefrom. Lastly, stitch the seam together in a spaced relationship.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
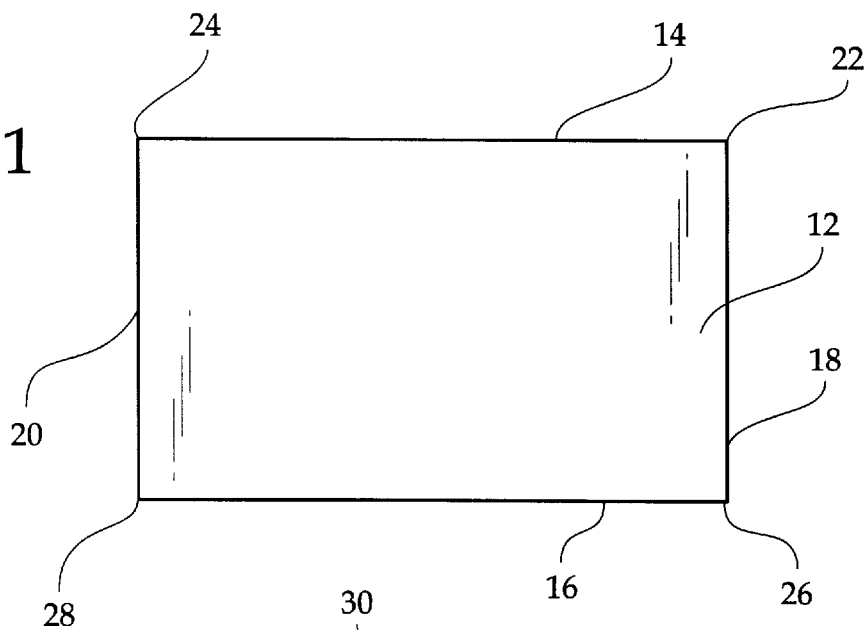
FIG. 1 is an illustration of a first step in the construction of the present invention.
Figure 2:
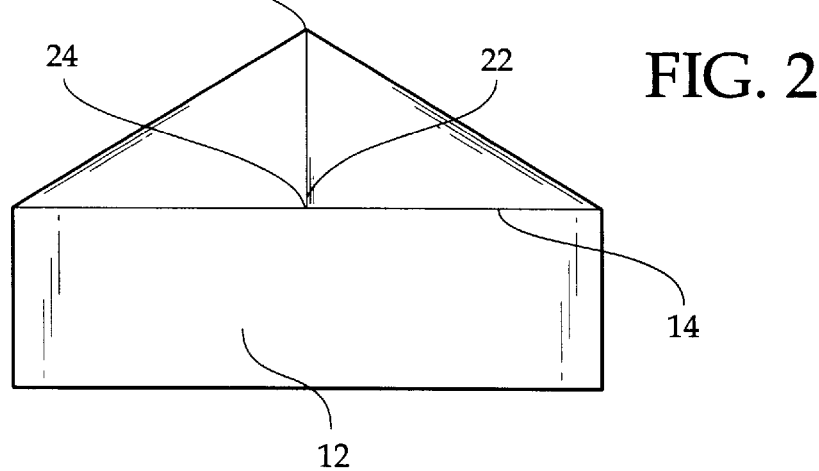
FIG. 2 is an illustration of a second step in the construction of the present invention.
Figure 3:
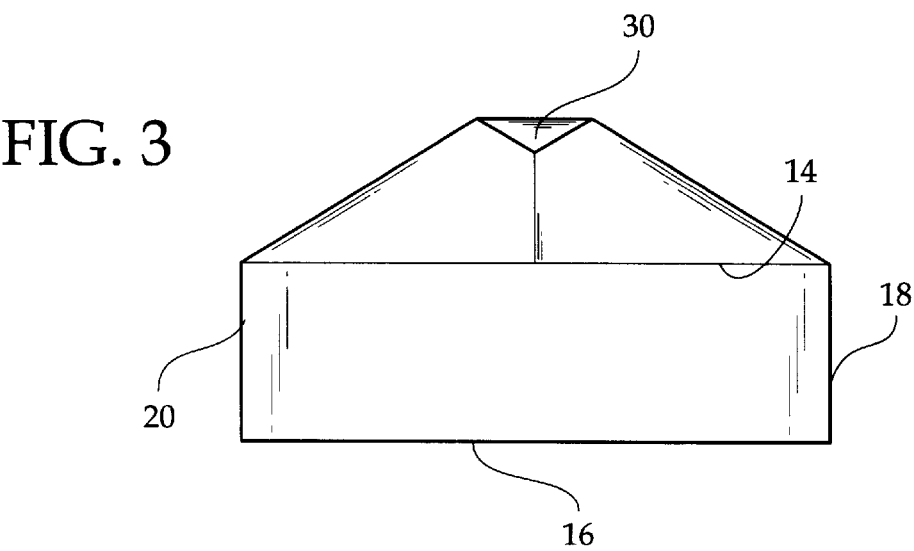
FIG. 3 is an illustration of a third step in the construction of the present invention.
Figure 4:
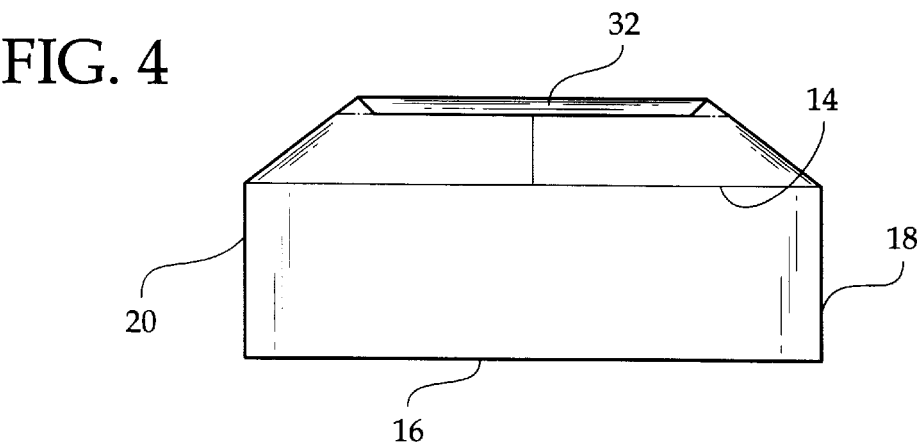
FIG. 4 is an illustration of a fourth step in the construction of the present invention.
Figure 5:
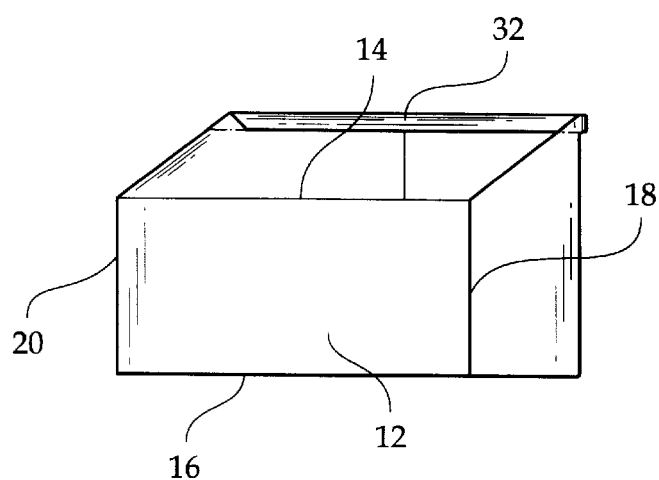
FIG. 5 is an illustration of a fifth step in the construction of the present invention.
Figure 6:
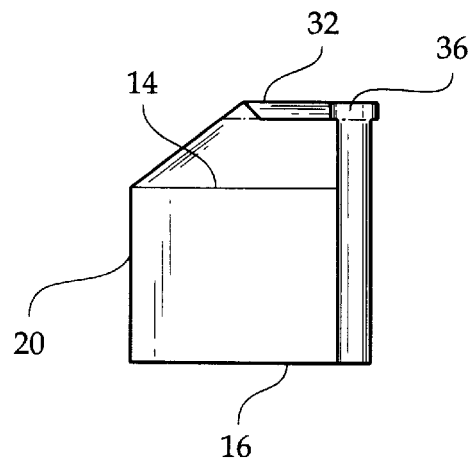
FIG. 6 is an illustration of a sixth step in the construction of the present invention.
Figure 7:
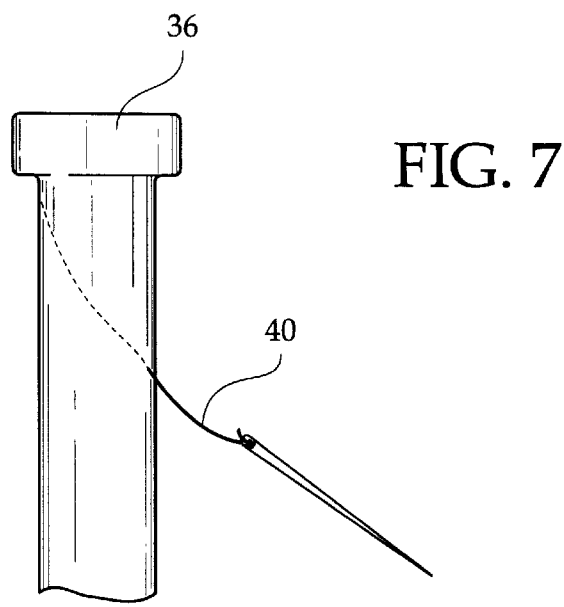
FIG. 7 is an illustration of a final step in the construction of the present invention.
Figure 8:
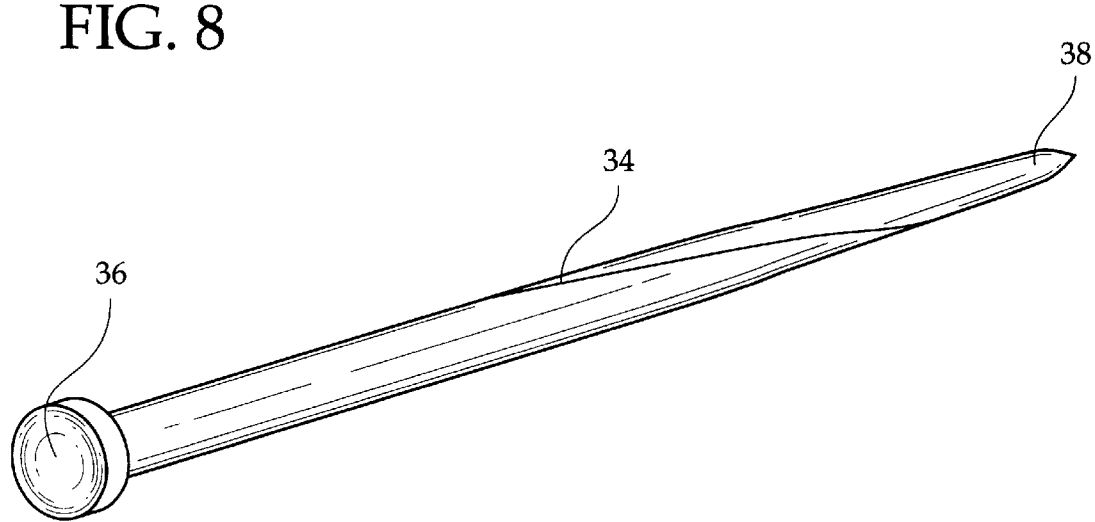
FIG. 8 is a perspective view of the preferred embodiment of the tension relieving towel and method of making constructed in accordance with the principles of the present invention.

With reference now to the drawings, and in particular, to FIGS. 1 through 8 thereof, the preferred embodiment of the new and improved tension relieving towel and method of making embodying the principles and concepts of the present invention and generally designated by the reference number 10 will be described.

Specifically, it will be noted in the various Figures that the device relates to a tension relieving towel and method of making for relieving tension in selected body areas. In its broadest context, the device consists of a rectangular towel that is folded and manipulated into a massaging instrument.

The rectangular towel 12 has opposed long upper and lower edges 14,16 and opposed short right and left edges 18,20. The towel 12 further includes opposed upper right and left corners 22,24 and opposed lower right and left corners 26,28. The rectangular towel 12 is then laid on a flat recipient surface. Note FIG. 1. Next, fold the upper right and left corners 22,24 downwardly whereby the upper edge 14 is folded in half within the towel 12 whereby an upper peak 30 is formed. Note FIG. 2. Next, fold the upper peak 30 downwardly. Note FIG. 3. Next, roll the upper peak 30 downwardly about eight revolutions to form a round roll 32. Note FIG. 4. Next, fold the right side 18 of the towel 12 inwardly. Note FIG. 5. Next, roll the right side 18 of the towel 12 inwardly until meeting the left side 20 to form a seam 34 whereby the round roll 32 forms a cap 36 with a tapered portion 38 extending downwardly therefrom. Note FIGS. 6–8. Lastly, stitch 40 the seam 34 together in a spaced relationship. Note FIG. 7.

Thus, a tension relieving instrument is formed. The tension can be varied simply be twisting the cap 36 in one direction while firmly holding the tapered portion 38.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A tension relieving towel and method of making for relieving tension in selected body areas comprising, in combination:

providing a rectangular towel having opposed long upper and lower edges and opposed short right and left edges, the towel further including opposed upper right and left corners and opposed lower right and left corners;

laying the rectangular towel on a flat recipient surface;

folding the upper right and left corners downwardly whereby the upper edge is folded in half within the towel whereby an upper peak is formed;

folding the upper peak downwardly;

rolling the upper peak downwardly about eight revolutions to form a round roll;

folding the right side of the towel inwardly;

rolling the right side of the towel inwardly until meeting the left side to form a seam whereby the round roll forms a cap with a tapered portion extending downwardly therefrom;

stitching the seam together in a spaced relationship.

2. A tension relieving towel and method of making for relieving tension in selected body areas comprising, in combination:

a rectangular towel having opposed long upper and lower edges and opposed short right and left edges, the towel further including opposed upper right and left corners and opposed lower right and left corners;

folding the upper right and left corners downwardly whereby the upper edge is folded in half within the towel whereby an upper peak is formed;

folding the upper peak downwardly;

rolling the upper peak downwardly a plurality of revolutions to form a round roll;

folding the right side of the towel inwardly;

rolling the right side of the towel inwardly until meeting the left side to form a seam whereby the round roll forms a cap with a tapered portion extending downwardly therefrom.

* * * * *